United States Patent [19]

Neuwirth et al.

[11] Patent Number: 5,501,681
[45] Date of Patent: Mar. 26, 1996

[54] INTRAUTERINE CRYOABLATION CAUTERIZING APPARATUS AND METHOD

[76] Inventors: Robert S. Neuwirth, 400 Gloucester St., Englewood, N.J. 07631; Lee R. Bolduc, 6416 Gainsborough Dr., Raleigh, N.C. 27612

[21] Appl. No.: 151,709

[22] Filed: Nov. 12, 1993

[51] Int. Cl.⁶ ............................................. A61B 17/00
[52] U.S. Cl. ........................... 606/21; 606/26; 606/22; 607/104; 607/105
[58] Field of Search ................. 606/20–26; 607/104, 607/105

[56] References Cited

U.S. PATENT DOCUMENTS

| | | | |
|---|---|---|---|
| 2,190,383 | 2/1940 | Newman | 607/105 |
| 2,190,384 | 2/1940 | Newman | 607/105 |
| 3,125,096 | 3/1964 | Antiles et al. | 606/22 X |
| 3,924,628 | 12/1975 | Droegemueller et al. | 606/21 |
| 4,397,314 | 8/1983 | Vaguine | 607/104 |
| 4,949,718 | 8/1990 | Neuwirth et al. | 607/105 |
| 5,084,044 | 1/1992 | Quint | 607/105 X |
| 5,195,965 | 3/1993 | Shantha | 607/105 X |
| 5,266,778 | 11/1993 | Bailey | 607/104 |

*Primary Examiner*—Peter A. Aschenbrenner
*Attorney, Agent, or Firm*—Kenyon & Kenyon

[57] ABSTRACT

A method and apparatus for effecting necrosis of a tissue lining of a mammalian body cavity, particularly a uterine endometrium, by introducing an applicator comprising a distendable bladder connected to a catheter into the uterus, distending the bladder by introducing a non-toxic fluid under pressure, cooling the fluid by means located internal to the bladder to a temperature below 32° F. for a period of about 4 to about 12 minutes and preferably about 6 minutes, thereby cauterizing substantially the entirety of the tissue lining, particularly the endometrium.

23 Claims, 6 Drawing Sheets

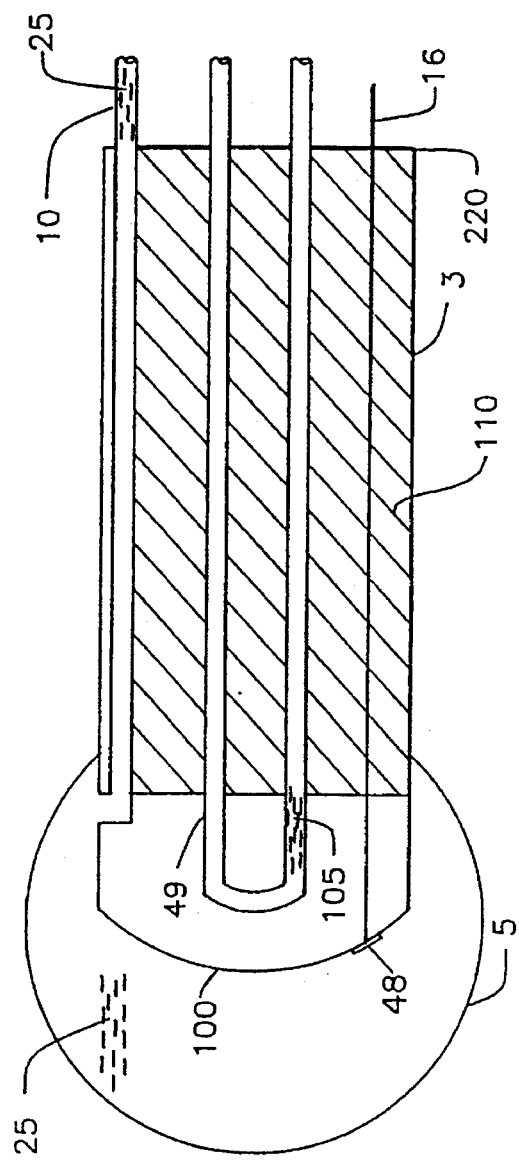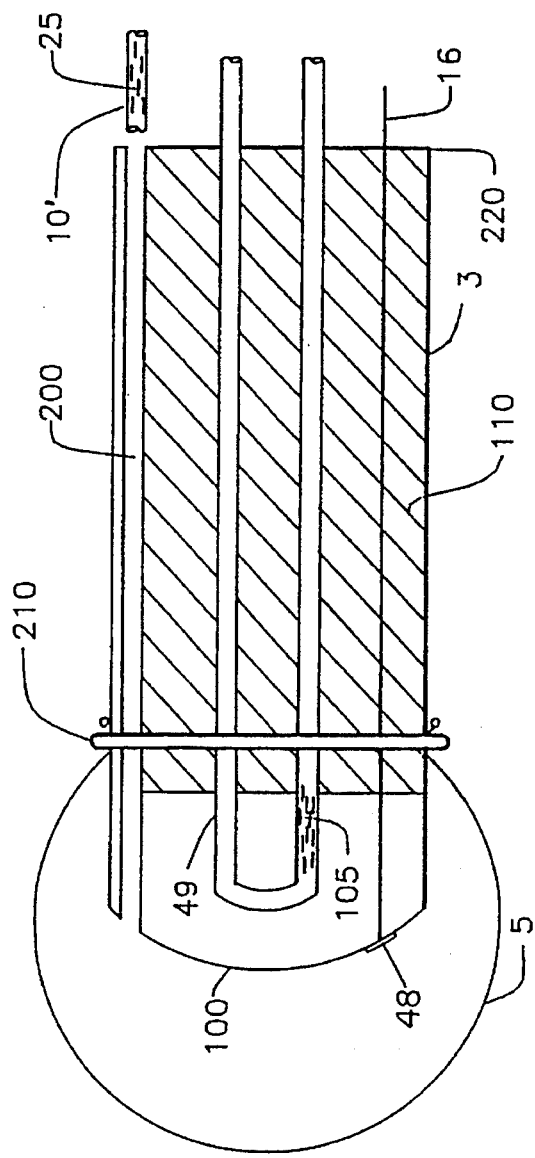

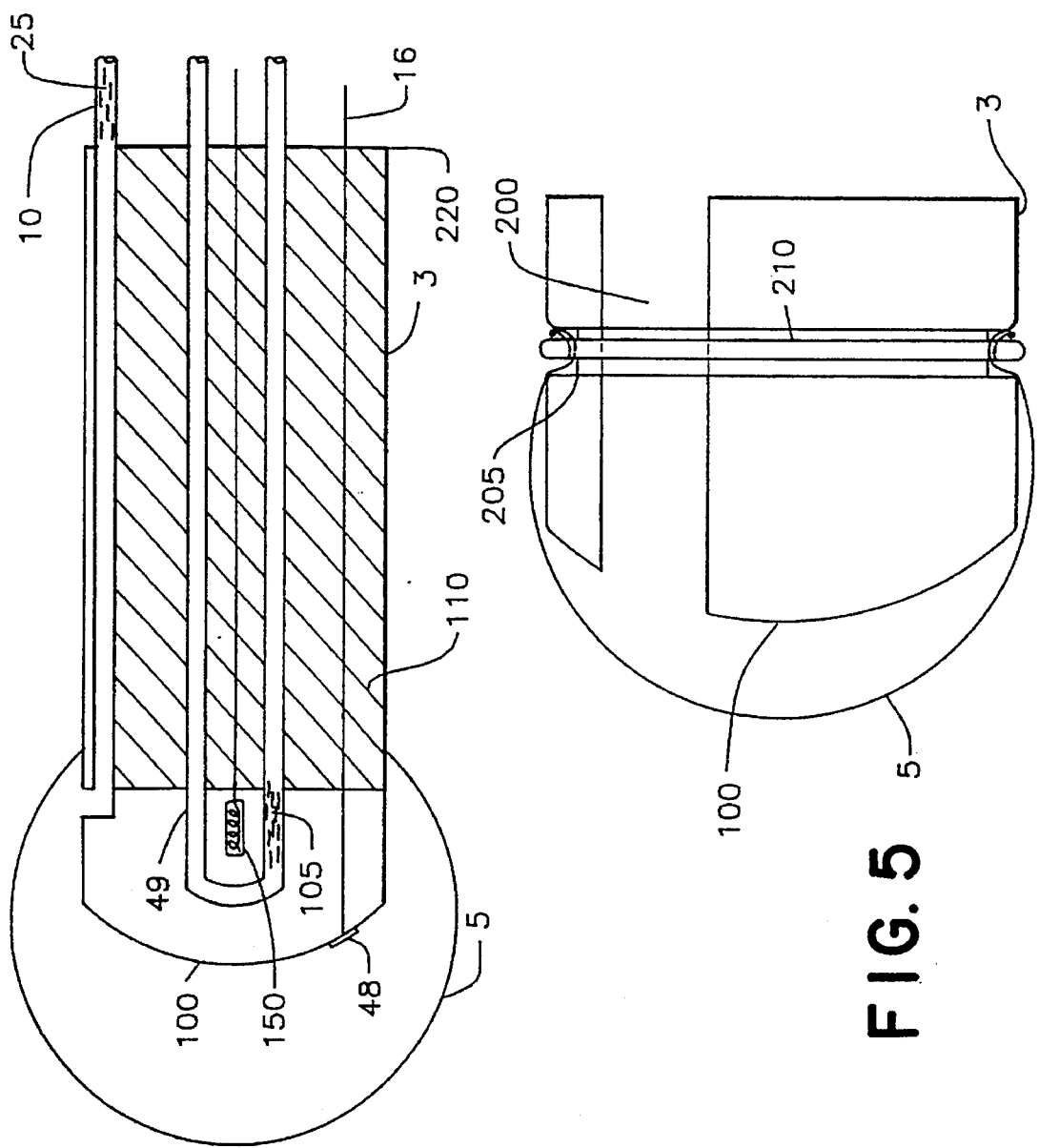

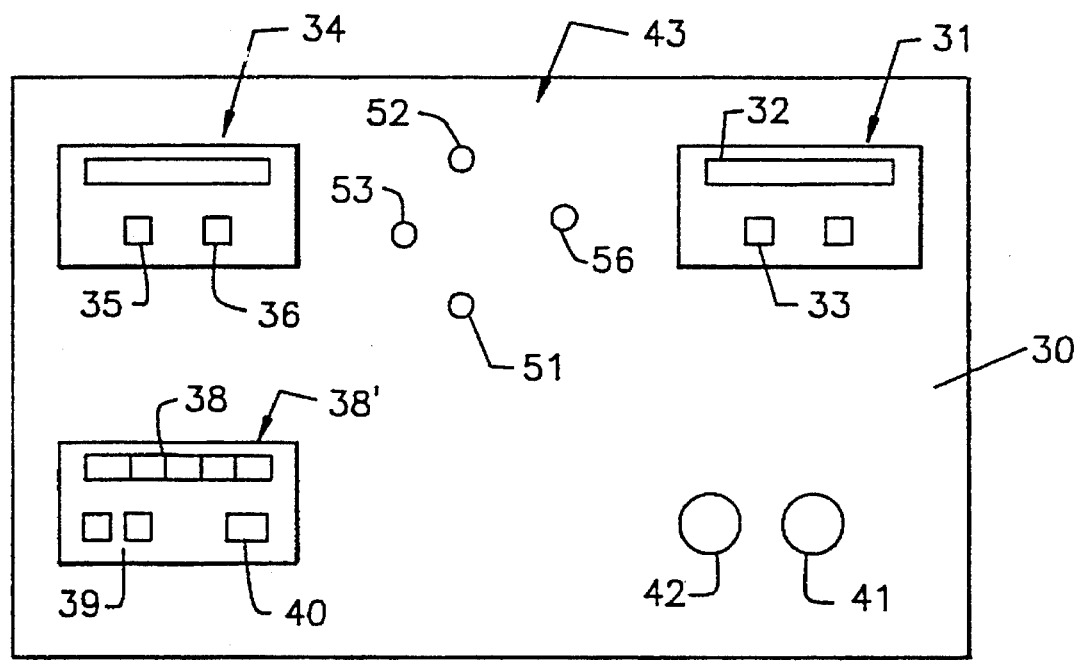
F I G. 7
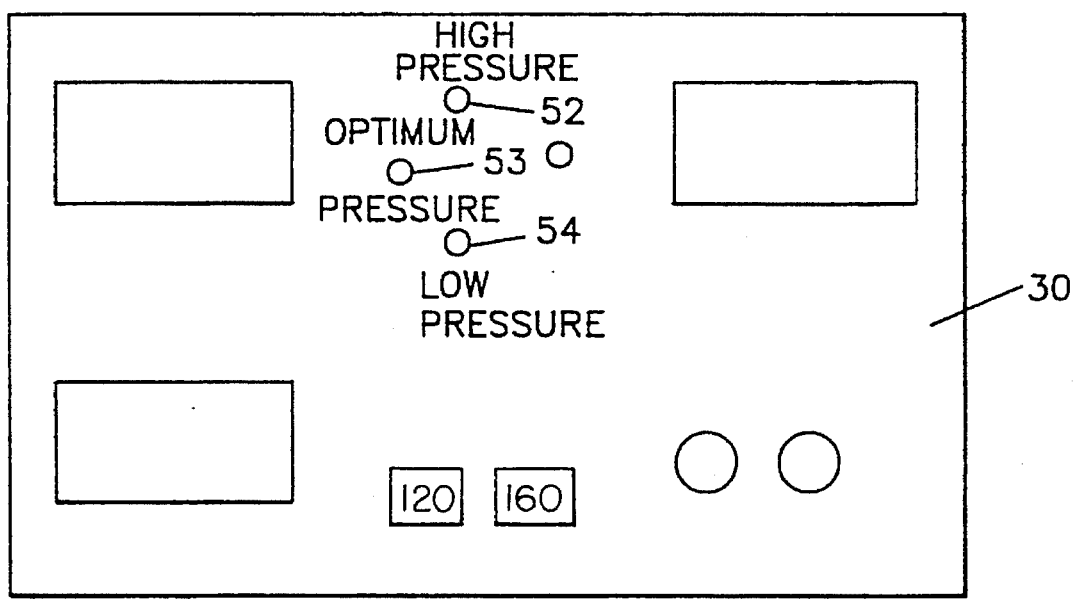
F I G. 8

INTRAUTERINE CRYOABLATION CAUTERIZING APPARATUS AND METHOD

BACKGROUND OF THE INVENTION

1. Field of the Invention

This invention relates to an apparatus and a method for cauterizing the tissue lining of a human body cavity, particularly the endometrium of the uterus. More specifically, the apparatus and method of the present invention ensures effective cauterization of the endometrium of a mammalian uterus without many of the disadvantages and dangerous features of known intrauterine cauterization techniques.

2. The Prior Art

The following terms as used herein have the meaning given below:

"Necrosis" means the death of cells in a tissue.

"Endometrium" is that portion of the inner lining of the uterus to which an embryo normally attaches and excludes the portions of the uterine inner lining forming the cervix, to which the embryo usually does not attach.

"Cryogenic" is used to refer to temperatures sufficiently low to cause necrosis.

Apparatus and methods for cauterization of the endometrium of a mammalian uterus, useful in sterilization procedures and cancer treatments, are well known. Thermal and cryogenic treatments have been utilized in such cauterization techniques and typically involve either the direct or indirect application of heat or cold to the tissue to be treated.

For example, a laser hysteroscope has been used to cauterize the endometrial layer of the uterus. This laser treatment suffers from several disadvantages. It requires the application of an intense amount of thermal energy to a relatively small area of tissue even though such a large amount of heat may not be necessary to effectively cauterize the tissue. Further, this laser treatment requires the physician to continually re-position the laser used in the treatment within the uterus in order to treat the entire endometrium. Such internal manipulation of a laser hysteroscope within the uterus of a patient is both difficult, requiring a significant level of skill to perform, and potentially dangerous. Accidental puncture of the uterine or tissue wall may result from manipulation of the laser scope within the uterus or body cavity, and tissue layers beneath the endometrium may be burned if a laser's beam is left focused on one area of tissue for too long a period of time.

A variety of alternatives to laser treatment in cauterizing the uterine endometrium are known. In U.S. Pat. No. 3,924,628, Droegemueller et al. disclose a method and apparatus for necrosing tissue cells that utilizes an extendable bladder which is inserted in the uterus and filled with a circulating fluid or gas at cryogenic temperatures (referring to temperatures sufficiently low to cause cell necrosis). The bladder disclosed by Droegemueller et al. is maintained in substantially continuous contact with the inner surface of the uterine lining and achieves necrosis of substantially all of the uterine endometrium in a single treatment. Droegemueller et al. disclose the use of liquid nitrogen that vaporizes prior to introduction into the bladder, thereby pressurizing the bladder to a level which ensures adequate contact with the uterus. Other fluids disclosed by Droegemueller et al. as useful in their method include refrigerants such as freon. Droegemueller et al.'s method and apparatus suffers from the disadvantage of employing cryogenic fluids which are toxic and could prove fatal to a patient in the event of bladder rupture. Moreover, Droegemueller et al.'s apparatus does not allow regulating the pressure used to inflate the bladder. In the event of a bladder rupture, the cryogenic fluid would rapidly change state from a liquid to a gas with possible grave consequences for the patient. Another disadvantage of Droegemueller et al.'s technique is that it does not limit the amount of cryogenic fluid that would be introduced into the uterus in the event of a bladder rupture.

In U.S. Pat. No. 2,734,508, Kozinski discloses a therapeutic apparatus for applying dry heat to body cavities comprising an applicator that is introduced in the body cavity while deflated and which is subsequently inflated and heated by means of circulating hot air. Kozinski does not disclose an applicator which conforms to the shape of a body cavity. Further, given the lower heat transfer coefficients of gases as compared with liquid, treatment with Kozinski's apparatus should involve a long period of time in order to achieve necrosis, thereby exposing the patient to additional discomfort and risk. Moreover, Kozinski's apparatus does not provide for measurement and regulation of internal pressures and temperatures of the applicator introduced.

U.S. Pat. No. 2,077,453, issued to Albright, discloses a therapeutic appliance comprising a relatively long tubular applicator which is shaped and formed generally to the passage into which it is to be inserted and which has relatively thin elastic rubber walls that transfer heat and which distend to fit irregularities of the treated areas upon application of internal pressure. Albright also discloses that fluids such as heated water could be utilized as a heating means in his applicator. The applicator of Albright, like that of Xozinski, however, suffers from the disadvantage that the distension of its walls to conform to the irregularities of the endometrium is limited as Albright provides an integral rubber web which serves to prevent undue distension of the applicator. Moreover, Albright requires that the fluid be circulated throughout the apparatus. Albright also does not provide an apparatus that allows regulation of temperature and pressure of the fluid or other bladder inflation means.

U.S. Pat. No. 3,369,549, issued to Armao, discloses a therapeutic device for applying heat or cold to body cavities comprising a capsule probe containing a heat exchanger and a flexible bladder that can be inflated to conform to a body cavity. Armao does not, however, disclose a control means for regulating the temperature and pressure of the flexible applicator, nor does he disclose cauterizing tissue in the cavity being treated.

Other patents that disclose the use of thermal treatment of the interior lining of a body cavity include U.S. Pat. Nos. 2,192,768; 2,466,042; 2,777,445; and 3,369,549.

SUMMARY AND OBJECTS OF THE INVENTION

It is an object of the present invention to provide a safe and efficacious method for cauterizing the tissue lining of a body cavity, particularly the endometrium of a uterus.

It is another object of the present invention to provide a relatively inexpensive and easy to replace applicator cooled by a controlled volume of a non-toxic fluid that can be used to effect cauterization of the uterine endometrium and which is controlled by means external to the applicator.

It is another object of the present invention to provide an apparatus for introducing a controlled volume of a non-toxic fluid under controlled pressure into the bladder and cooling the fluid while it is in a bladder within the uterus so as to assure substantially uniform contact of the bladder with the endometrium.

It is still another object of the present invention to provide an apparatus for regulating the temperature and pressure of the fluid in the bladder while the bladder is within the uterus.

The present invention also provides an apparatus for effecting necrosis of the tissue lining of a body cavity, and, in particular, Substantially the entirety of the endometrium of a mammalian uterus comprising an applicator which comprises a catheter for insertion into the uterus, the catheter having a proximal end and a distal end, and a distendable bladder attached to the proximal end; inflating means connected to the distal end for distending the distendable bladder; cooling means for cooling a non-toxic inflation medium introduced into the distendable bladder; and control means for regulating the distending of the distendable bladder and the temperature of the non-toxic inflation medium introduced into the distendable bladder.

The present invention provides a method for effecting cauterization necrosis of the tissue lining of a mammalian body cavity comprising the steps of inserting a distendable bladder attached to a length of rigid tubing into the body cavity; inflating the distendable bladder to a predetermined pressure with a non-toxic fluid so that the distendable bladder is in contact with substantially all of the tissue lining for which necrosis is desired; cooling the fluid to a temperature sufficient to effect cauterization necrosis; controlling the temperature and pressure of the fluid by control means connected to the distendable bladder and rigid tubing; and maintaining the bladder so inserted and inflated with the non-toxic fluid at a temperature for a period of time sufficient to effect cauterization necrosis of substantially all of the tissue lining of the body cavity for which necrosis is desired.

The present invention also provides a method for effecting cauterization necrosis of a uterine endometrium comprising the steps of inserting a distendable bladder attached to a length of rigid tubing into the uterus; inflating the distendable bladder to a predetermined pressure with a non-toxic fluid so that the distendable bladder is in contact with substantially all of the endometrium; cooling the fluid to a temperature sufficient to effect cauterization necrosis; regulating the temperature and pressure of the fluid by control means connected to the distendable bladder; and maintaining the bladder so inserted and inflated with the non-toxic fluid at a temperature for a period of time sufficient to effect cauterization necrosis of substantially all of the uterine endometrium.

The present invention further provides a method for cauterizing substantially the entirety of the endometrium of a mammalian uterus by application within an inflatable bladder of a fluid at a pressure of 40 to 140 mmHg and preferably about 80 mmHg, cooled toga temperature below 32° F. for a period of about 4 to 12 minutes, with a preference of about 6 minutes, thereby realizing substantial necrosis of substantially all of the uterine endometrium without significant damage to surrounding tissue.

These and other objects of the present invention are achieved by a method in which necrosis of the endometrium of a mammalian uterus may be achieved by insertion of an applicator comprising rigid and flexible tubing and a readily distendable high strength bladder material into the uterus; introduction of a non-toxic fluid through the tubing into the distendable bladder at a pressure of 40 to 140 mmHg and preferably about 80 mmHg, thereby inflating the bladder so that it substantially conforms to the irregularities in the shape of the endometrium; measuring and regulating the pressure of the fluid by means external to the uterus; cooling the fluid to a temperature below 32° F., for a period of about 4 to 12 minutes, with a preference of about 6 minutes, thereby cauterizing substantially the entirety of the uterine endometrium.

BRIEF DESCRIPTION OF THE DRAWINGS

FIG. 3 is a cutaway view of an applicator and distendable bladder constructed in accordance with the invention;

FIG. 4 is a cutaway view of an alternative embodiment of an applicator and replaceable distendable bladder constructed in accordance with the invention;

FIG. 5 is a detailed view of a portion of the embodiment shown in FIG. 4;

FIG. 7 depicts a system control unit;

FIG. 8 is a detail view of a pressure limiting and safety monitor;

FIG. 10 is a cutaway view of an alternative embodiment of an applicator and distendable bladder constructed in accordance with the invention.

DESCRIPTION OF A PREFERRED EMBODIMENT

Figure 1:
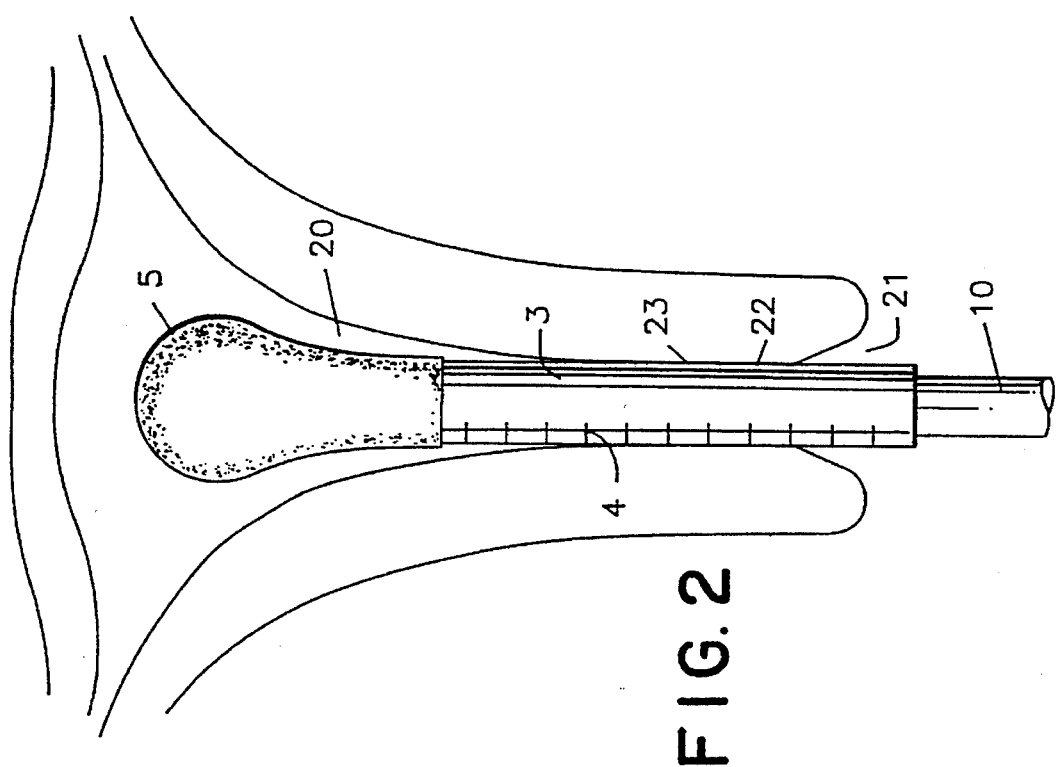
FIG. 1 depicts an applicator and a distendable bladder utilized in the method of the present invention which has been inserted into and inflated within a mammalian uterus.

FIG. 1 shows an inflated distendable bladder 5 attached to rigid tubing 3 having a distal end 100 and a proximal end 220 located within a mammalian uterus 6. Inflation of the distendable bladder 5 with a fluid 25 assures uniform contact of the bladder 5 with the endometrial tissue layer 27 of mammalian uterus 6.

The rigid tubing 3 and the attached distendable bladder 5 must be sufficiently small, when the distendable bladder is deflated, so that it can be conveniently and safely inserted into the uterus 6 through a partially dilated cervix 22. The rigid tubing with the deflated bladder is aligned with the cervical canal after the cervix is exposed with a speculum and grasped with a tenaculum. After the distendable bladder 5 has been inserted, the distendable bladder 5 should be inflated to a pressure sufficient to ensure firm contact with the tissue to be necrosed, in this case the endometrial tissue layer on the interior uterine surface, but should preferably be maintained at a pressure at or about 40 to 140 mmHg, and preferably about 80 mmHg, to minimize risk of rupture of the distendable bladder 5 and possible internal injury to the patient.

Distendable bladder 5 must be capable of withstanding low temperatures without rupturing, and preferably have as good a heat transfer characteristic as is obtainable in such materials to provide efficient cooling action. A distendable bladder of a heat curing rubber such as latex has been found satisfactory.

Fluid 25 preferably should be a sterile non-toxic fluid with a freezing point of about 32° F. A sterile saline solution has been found satisfactory.

Figure 2:
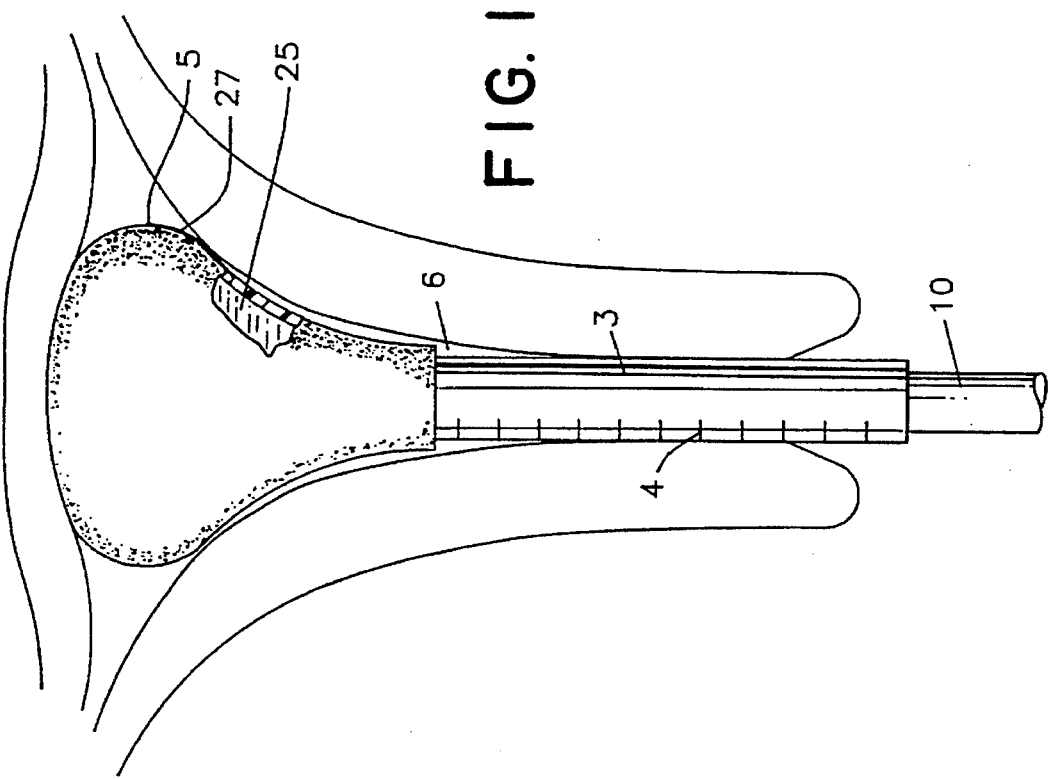
FIG. 2 depicts placement of the applicator and distendable bladder within a mammalian uterus.

As illustrated in FIG. 2, the uninflated distendable bladder 5 attached to rigid tubing 3 is inserted into the vagina 21, past the cervical os 22, through the cervical canal 23, for placement in the uterine cavity 20. Placement may be aided by virtue of scale gradations 4 located on the rigid tubing 3 to indicate the depth of insertion of the bladder 5. Rigid tubing 3 is attached to a control unit 30 (shown in FIGS. 6 to 9) via flexible tubing 10, cooling conduit 49, and thermocouple lead 16.

FIG. 3 is a cutaway view of an inflated distendable bladder 5 attached to rigid tubing 3, wherein coolant conduit 49 provides refrigerant 105 from system control unit 30 to the distal end 100 of rigid of tubing 3 causing the fluid 25 within the bladder 5 which is in contact with the external surface of the distal end 100 of rigid tubing 3 to cool and freeze. In this embodiment, flexible tubing 10 is integrally formed with rigid tubing 3. Rigid tubing 3, coolant conduit 49, and related couplings should be constructed of a materials well known to those skilled in the art which are capable of withstanding the high pressure produced by the refrigerant 105 circulating through the coolant conduit 49. Rigid tubing 3 may be constructed from a wide range of materials well known to those skilled in the art as suitable for this purpose, however, in a preferred embodiment rigid tubing 3 is constructed of stainless steel because of its strength and thermal conductivity. In an especially preferred embodiment, insulation 110 surrounds coolant conduit 49 so as to keep the refrigerant 105 at a low temperature and protect the non-target tissue in contact with the external surface of rigid tubing 3. The temperature of the fluid 25 is measured by thermocouple 48 and the reading is transmitted via thermocouple lead 16 to control unit 30 where it is displayed at temperature display 32.

FIG. 4 shows an alternative embodiment of the apparatus shown in FIG. 3 in Which rigid tubing 3 is provided with a longitudinal bore 200 in fluid communication with the interior of bladder 5. Longitudinal bore 200 is sized to receive and is adapted to form a substantially fluid tight seal with tubing 10' for introducing saline 25 into bladder 5. As shown in greater detail in FIG. 5, a flexible securing means 210 is sized to fit into securing groove 205 on rigid catheter 3. Securing means 210 is also sized to exert pressure on rigid tubing 3 sufficient to form a substantially fluid tight seal between the bladder 5 and tubing 3 when bladder 5 is positioned between securing means 210 and rigid tubing 3.

Figure 6:
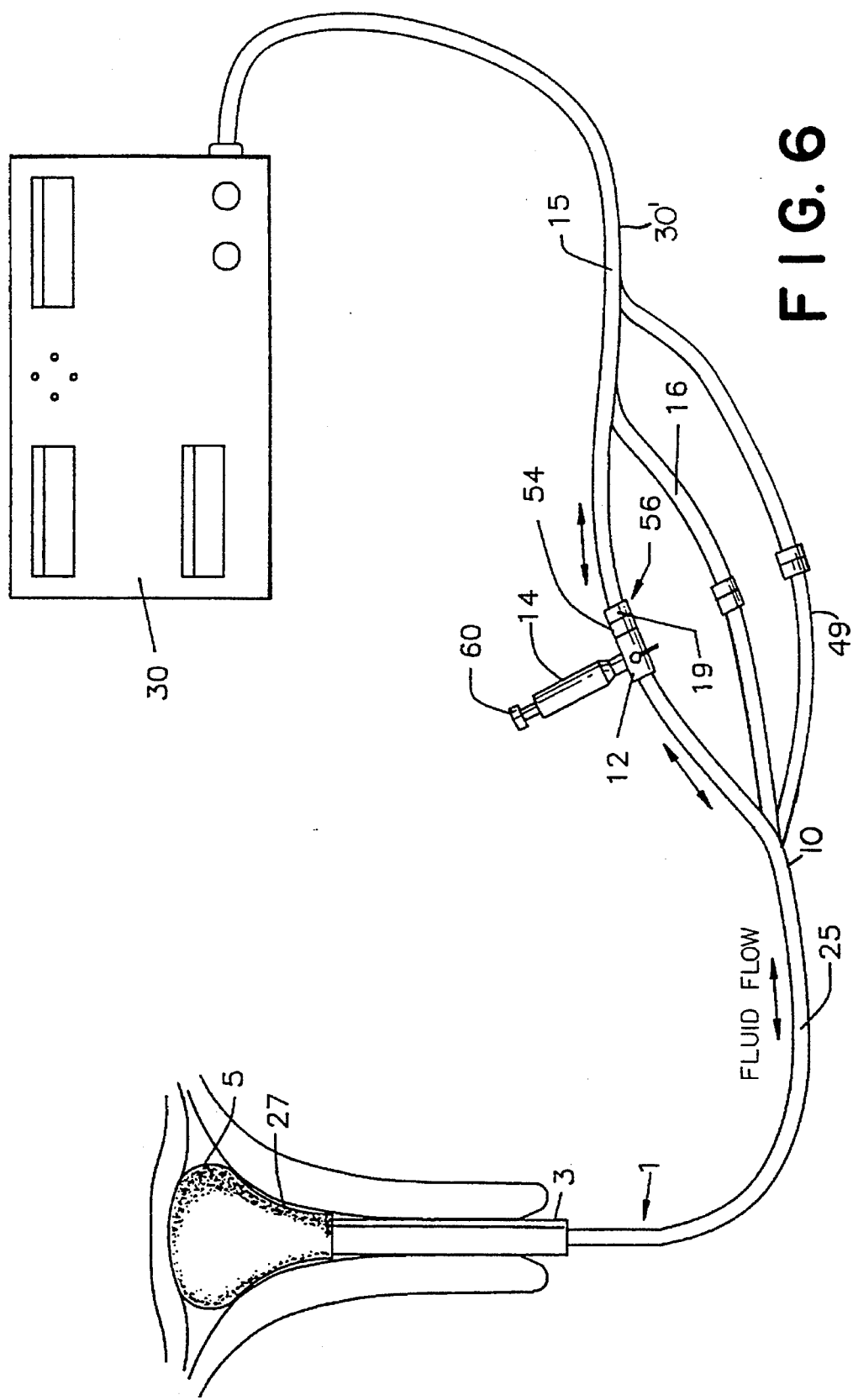
FIG. 6 is a view of an apparatus constructed in accordance with the invention.

FIG. 6 depicts the arrangement of control unit 30 and applicator end 1, comprising the distendable bladder 5, rigid tubing 3 and flexible tubing 10, coolant conduit 49, thermocouple lead 16, and the interconnection of those elements. A fluid system comprises that portion of the invention through which the fluid 25 travels, including a hypodermic barrel 14 or other fluid source (not shown), flexible tubing 10, rigid tubing 3, distendable bladder 5 and control unit 30. Manipulation of the hypodermic barrel 14 enables the operator of the system to control the amount of fluid 25 in the fluid system, inflation and deflation of the distendable bladder 5 by adding or removing fluid, respectively, and pressure of the fluid 25 in the system. Hypodermic barrel 14 also provides protection for the patient by allowing fast and safe reduction of excessive pressures in the system that might build up through some malfunction.

Manipulation of the hypodermic barrel 14 by depressing a plunger 60 causes fluid 25 to be introduced through 3-way stopcock 12 into the flexible tubing 10 and into the bladder 5. The fluid 25 emerges from flexible tubing 10 and enters into distendable bladder 5, forcing distendable bladder 5 to expand into contact with the endometrial tissue layer 27 of the uterus 6. The fluid 25 is also directed along the flexible tubing 10 to the control unit 30 allowing measurement of the fluid pressure within the bladder by well known means. Flexible tubing 10 may traverse rigid tubing 3, as shown in FIG. 3, and be in fluid communication with the interior of bladder 5. Alternatively, flexible tubing 10 may be connected to the proximal end 220 of rigid tubing 3 and form a substantially fluid tight seal with longitudinal bore 200 in rigid tubing 3.

Each of the parts of the fluid system is in fluid communication providing constant fluid pressure within the entire fluid system and allowing measurement of the pressure at the applicator end 1 via measurement of pressure of the end attached to the control unit 30.

Flexible tubing 10 is connected to a fluid joint 56 via pressure transducer 54, by well known means. Using a standard luer lock connector 19, pressure transducer 54 and hypodermic barrel 14 are connected to flexible tubing 10 via a readily available 3-way stopcock 12. 3-way stopcock 12 may be used to isolate the hypodermic barrel 14 or other fluid source from the fluid System once the desired fluid pressure is reached.

FIGS. 7 and 8 depict control unit 30, consisting of fluid temperature control 31, fluid pressure control 34, time control 38' and a power source (not shown). The control unit 30 includes a power switch 42 and fuse 41. Fluid temperature is regulated by fluid temperature control 31 and is set by temperature set/reset button 33. The temperature of fluid 25 in the distendable bladder 5 is measured by thermocouple 48, transmitted via thermocouple lead 16, and is shown at temperature display 32.

Fluid pressure within the fluid system is regulated by means of controls located on fluid pressure control panel 34. The upper limit for fluid pressure is controlled by high pressure set/reset button 35, with the lower limit controlled by low pressure set/reset button 36. Fluid pressure in mmHg is shown by LED pressure display 37. Control unit 30 also has pressure indicator display 43, which upon introduction of fluid 25 into the fluid system provides an easy to see visual display of fluid pressure within the fluid system.

Time for the procedure is shown at time display 38, which displays both lapsed time and time remaining for the procedure. Total time for the procedure may be easily set in minutes, seconds, and tenths of seconds using time set buttons 39 and may be cleared or reset using time clear/reset button 40.

In operation, the fluid pressure is adjusted to a pressure which is less than the optimum pressure to allow for the expansion of the fluid and the increase in volume and pressure which will result when the fluid 25 freezes. The pressure indicator display 43 is comprised of a low pressure indicator 51, a high pressure indicator 52 and an optimum pressure indicator 53. As fluid 25 is introduced into the fluid system by manipulation of hypodermic barrel 13, the pressure indicator display 43 is successively illuminated as various fluid pressures are reached. Low pressure indicator 51 is illuminated when fluid pressure is below the preset range. High pressure indicator 52 is illuminated when fluid pressure is above the preset range. Optimum pressure indicator 53 is illuminated when fluid pressure is within the preset range.

These indicators allow the practitioner to readily reach the preset pressure range by varying the amount of fluid in the fluid system via manipulation of the hypodermic barrel 14. A separate cooling medium control 120 is also provided to indicate when power is being provided to circulate a cooling medium through coolant conduit 49. In an alternative embodiment, the cooling medium control 120 may be adapted to drain coolant from coolant conduit 49 and circulate in its place saline at a temperature higher than 32° F. to melt the frozen fluid 25 in bladder 5 when the procedure is complete.

Figure 9:
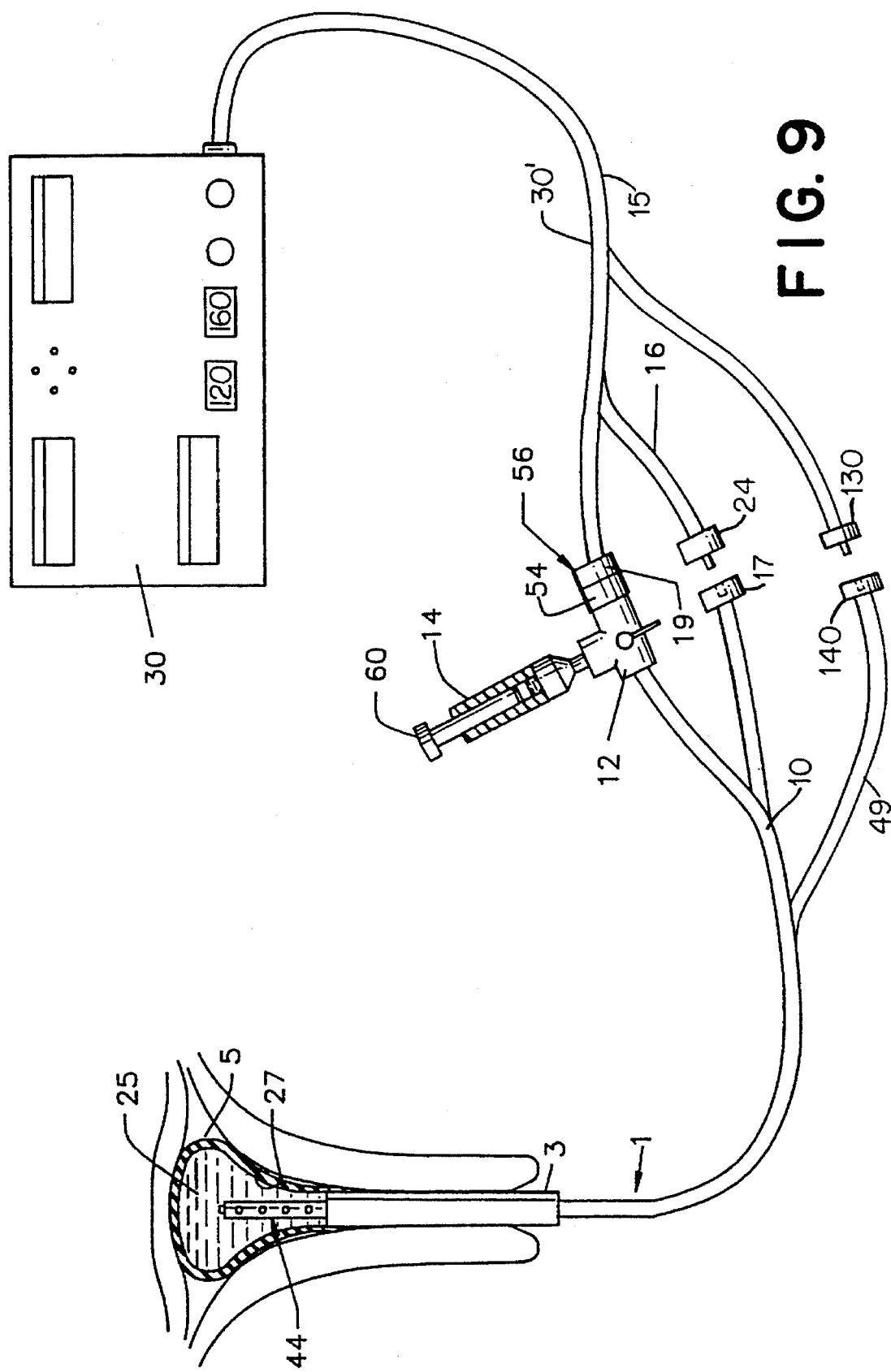
FIG. 9 depicts a means for connecting and disconnecting the applicator.

The applicator end 1 is designed to be easy to replace as shown in FIG. 9, which depicts control unit end 30' and applicator end 1 of the invention. Control unit end 30' is composed of lead 16 which is attached on one end to control unit 30 and on the o her end to male electrical connector 24, which allows transmittal of temperature readings from the thermocouple 48. Male electrical connector 24 is readily attached or disattached to female electrical connector 17 on the applicator end 1.

Control unit end 30' is also comprised of components from the fluid system including flexible tubing 10 attached to 3-way stopcock 12. 3-way stopcock 12 provides control over the introduction and removal of fluid 25 via hypodermic barrel 14. The applicator end 1 is easily connected or disconnected from the 3-way stopcock via a luer lock connector 19 attached to pressure transducer 54.

Control unit end 30' is also comprised of the cooling system including coolant conduit 49 to allow for the introduction and removal of a cooling medium 105 into and from rigid tubing 3 via the cooling medium control 120 on control panel 30. Cooling conduit 49 is attached on one end to control unit 30 and on the other end to male connector 130. Male connector 130 is readily attached or disattached to female connector 140 which allows transmittal of the refrigerant 105 from control panel 30 into rigid tubing 3. The components of the cooling system are made of materials well known by those skilled in the art as suitable for the high pressures and low temperatures to which they are subjected. The invention will now be illustrated by the following example.

Example

The cauterization procedure is preceded by screening against cancer of the affected region and physical condition within established norms. A PAP smear and endometrial biopsy/ curettage must exclude cancer or precancerous lesions of the uterus and cervix. If a fibroid uterus is present, an ultrasound should exclude ovarian masses. The uterine cavity must be 10 cm or less in length to be suitable for the small distendable bladder size.

The patient should be post menstrual or start on Danazol, or the equivalent which causes reduction in bleeding and a thin endometrium, at a rate of 800 ml daily, from the 5th day of the previous menstrual period until two weeks after the procedure. She will undergo the procedure in the ambulatory surgery unit or out-patient facility where Valium and/or Demerol can be given intravenously if there is pain during the heating phase of the procedure.

The applicator will be inserted after a bimanual examination and speculum of the cervix. Dilation to 6 mm. may be required which may necessitate a local 1% lidocaine block of the cervix. Once in place the applicator stem (rigid tubing) protrudes from the vagina. Placement of the applicator may be facilitated by distance markings on the rigid tubing indicating depth of insertion.

Upon placement of the applicator it will be connected to a control unit via attachment of the thermocouple lead, flexible tubing, and coolant conduit protruding from the rigid tubing and connected to their counterparts extending from the control unit.

Subsequent to insertion of the applicator, the control unit will be powered on in order to allow the practitioner to set the system constraints. The temperature of the fluid in the bladder will be set at the temperature control panel and can be measured via the thermocouple located within the bladder. Fluid pressure constraints are set at the pressure control panel, and upon inflation of the distendable bladder by introduction of fluid to the fluid system by depressing the plunger on the hypodermic barrel, can be easily measured by looking at the pressure indicator lights located on the control unit. The fluid volume and pressure will be adjusted to allow for the increase in volume and pressure which will result when the fluid freezes.

The practitioner then proceeds to inflate the distendable bladder by rotating the lever on the 3-way stopcock in order to access the fluid source and depressing the plunger on the hypodermic barrel which may serve as the fluid source. The practitioner injects the fluid into the fluid system until the pressure indicator lights indicate that the fluid pressure is within the pre-set constraints. At that point, the practitioner manipulates the 3-way stopcock to close off access to the fluid system by the fluid remaining in the hypodermic barrel. Thus, the fluid is non-circulating during the cooling portion of the procedure. The volume of fluid necessary to inflate the bladder will vary from 3 to 20 ml in most cases in order to reach the volume and pressure wherein the bladder is substantially in contact with all of the endometrium when the fluid is frozen.

The practitioner then activates the cooling medium control causing a pump (not shown) to pump refrigerant through the cooling conduit into the applicator. The refrigerant circulating through the rigid tubing draws heat from the fluid in the bladder and freezes the fluid in the bladder. Once the desired temperature level is reached, the system timer is activated to time the procedure and provide automatic turn off of the cooling medium control at the end of a preset period.

Upon completion of the procedure, the fluid is allowed to melt and the 3-way stopcock is again manipulated to allow the fluid to be withdrawn from the fluid system causing the distendable bladder to deflate.

In an alternative embodiment, saline having a temperature greater than 32° F. is pumped into the fluid conduit to facilitate melting of the frozen fluid. In still another embodiment, a resistive heating element 150, shown in FIG. 10, is disposed in the tip of the applicator and is energized to speed the melting of the frozen fluid. The heating element is controlled from heating element control 160 on control panel 130. The heating element control may be provided with a timing means and a temperature control means.

In yet another embodiment, at the completion of the procedure, a catheter is inserted between the applicator and the cervix and saline having a temperature greater than 32° F. is introduced so as to bathe the external surface of the bladder and facilitate the melting of the frozen fluid within the bladder.

Upon deflation of the distendable bladder, the applicator may be safely withdrawn from the patient. The coagulated endometrium is then removed from the endometrial cavity with a curette, leaving the underlying surface free to form adhesions with the other opposing surfaces of the endometrial cavity. The fluid connections are then disconnected and, depending Upon the embodiment of the invention utilized, the applicator and bladder may be discarded and a new one used for subsequent treatments. If the embodiment utilizing the removable bladder is used, the securing means is loosened, the bladder is removed and discarded, the applicator is sterilized, and a new bladder is placed and secured on the applicator for subsequent use.

What is claimed is:

1. An apparatus for effecting necrosis of an uterine endometrium comprising:

an applicator comprising a catheter for insertion into the uterus, said catheter having a proximal end and a distal end, and a distendable bladder attached to said distal end;

inflating means connected to said proximal end for distending said distendable bladder;

cooling means disposed within said distal end of said catheter and connected to said proximal end for cooling a non-circulating fluid within said distendable bladder; and control means communicating with said inflating means and said cooling means for regulating the distending and cooling of said non-circulating fluid within said distendable bladder.

2. The apparatus of claim 1, wherein said catheter is comprised of:

a first fluid conduit disposed within paid catheter having a proximal end and a distal end, said distal end in fluid communication with the interior of distendable bladder, and said proximal end in fluid communication with said inflating means;

a second fluid conduit having an entry port and an exit port disposed at said proximal end of said catheter, said entry and exit ports in fluid communication with said cooling means.

3. The apparatus of claim 2, wherein said inflating means comprises a fluid and a first pump means connected to said first fluid conduit for pumping said fluid through said first fluid conduit and into said distendable bladder.

4. The apparatus of claim 3, wherein said cooling means comprises a refrigerant and a second pump means in fluid communication with said entry port and said exit port of said second fluid conduit for circulating a liquid cooling medium through said catheter.

5. The apparatus of claim 4, wherein said control means is external to the uterus and connected to said first fluid conduit, said second fluid conduit.

6. The apparatus of claim 3, wherein said pumping means comprises a hypodermic barrel connected to said first fluid conduit.

7. The apparatus of claim 6, wherein said hypodermic barrel is connected to said first fluid conduit by a three-way valve.

8. The apparatus of claim 1, further comprising means for disengaging said applicator from said control means so that the applicator and the control means may be separated.

9. The apparatus of claim 1, wherein said distendable bladder is capable of resisting an internal pressure of at least 300 mmHg and a temperature below 32° F. without rupturing.

10. The apparatus of claim 9, wherein said distendable bladder is comprised of latex rubber.

11. The apparatus of claim 2, wherein said catheter is comprised of stainless steel.

12. The apparatus of claim 1, wherein said control means comprises:

volume control means;

temperature control means;

pressure control means; and time control means.

13. The apparatus of claim 12, wherein said temperature control means comprises:

a thermocouple internal to said distendable bladder for measuring the temperature of said fluid; and a temperature display attached to said thermocouple by at least one wire;

said temperature display further providing a means for setting the temperature of said cooling means.

14. The apparatus of claim 12, wherein said pressure control means comprises:

a pressure sensor connected to said applicator by said first fluid conduit; and a pressure display attached to said first fluid conduit tubing;

said pressure display further providing a means for setting the pressure of said inflating means.

15. The apparatus of claim 12, wherein said time control means comprises a clock.

16. The apparatus of claim 15, wherein said clock is programmable and connected to said temperature control means.

17. The apparatus of claim 1, further comprising a indicating the positioning of means for positioning said distendable bladder in the uterus.

18. The apparatus of claim 17, wherein said positioning means comprises scale gradations on said catheter for indicating depth of insertion of said distendable bladder into the uterus.

19. The apparatus in any one of the preceding claims further comprising a heating element disposed at the distal end of said catheter.

20. A method for effecting cauterization necrosis of the tissue lining of a mammalian body cavity comprising the steps of:

(a) inserting a distendable bladder into the body cavity;

(b) inflating said distendable bladder to a predetermined pressure with a non-circulating non-toxic fluid so that said distendable bladder is in contact with substantially all of the tissue lining for which necrosis is desired;

(c) cooling said non-toxic fluid to a cryogenic temperature;

(d) controlling the temperature and pressure of said fluid by control means connected to said distendable bladder; and (e) maintaining said bladder so inflated with said fluid at a temperature for a period of time sufficient to effect cauterization necrosis of substantially all of the tissue lining of the body cavity for which necrosis is desired.

21. A method as described in claim 20, wherein the exterior of said distendable bladder in contact with the tissue lining is maintained at a temperature below 32° F. for a period of time of from about 4 to about 12 minutes, and preferably about 6 minutes.

22. A method for effecting cauterization necrosis of an uterine endometrium comprising the steps of:

(a) inserting a distendable bladder into the uterus;

(b) inflating said distendable bladder to a predetermined pressure with a non-circulating non-toxic fluid so that said distendable bladder is in contact with substantially all of the endometrium;

(c) cooling said non-toxic fluid to a cryogenic temperature;

(d) regulating the temperature and pressure of said fluid by control means connected to said distendable bladder; and (e) maintaining said bladder so inflated with said fluid at a temperature for a period of time sufficient to effect cauterization necrosis of substantially all of the uterine endometrium.

23. A method as described in claim 22, wherein the exterior of said distendable bladder in contact with the endometrium is maintained at a temperature below 32° F. for a period of time of from about 4 to about 12 minutes, and preferably about 6 minutes.

\* \* \* \* \*